US008889038B1

(12) United States Patent
Anderson et al.

(10) Patent No.: US 8,889,038 B1
(45) Date of Patent: Nov. 18, 2014

(54) WOOD PRESERVATIVES CONTAINING COPPER COMPLEXES

(75) Inventors: Albert Gordon Anderson, Wilmington, DE (US); Mark A. Scialdone, West Grove, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 692 days.

(21) Appl. No.: 12/338,548

(22) Filed: Dec. 18, 2008

Related U.S. Application Data

(60) Provisional application No. 61/014,820, filed on Dec. 19, 2007.

(51) Int. Cl.
| C09K 3/00 | (2006.01) |
| C23F 11/00 | (2006.01) |
| A01N 25/34 | (2006.01) |
| A01N 25/00 | (2006.01) |
| C09D 5/16 | (2006.01) |
| C09D 5/18 | (2006.01) |
| A01N 55/02 | (2006.01) |
| A61K 31/315 | (2006.01) |
| A61K 31/28 | (2006.01) |
| B05D 1/28 | (2006.01) |
| D21C 3/20 | (2006.01) |
| D21C 3/00 | (2006.01) |
| B32B 23/08 | (2006.01) |
| B32B 27/06 | (2006.01) |
| B32B 27/10 | (2006.01) |

(52) U.S. Cl.
USPC ............. 252/389.53; 252/389.32; 252/384; 252/385; 424/404; 424/405; 106/18.27; 514/494; 514/499; 427/439; 427/440; 162/72; 162/79; 428/508; 428/511

(58) Field of Classification Search
USPC ........ 252/389.32, 389.53, 384, 385; 424/404, 424/405; 106/18.27; 514/494, 499; 427/439, 440; 162/72, 79; 428/508, 428/511

See application file for complete search history.

(56) References Cited

U.S. PATENT DOCUMENTS

| 3,345,344 | A | | 10/1967 | Fetscher et al. |
| 3,629,446 | A | * | 12/1971 | Frohberger et al. ............ 514/494 |
| 4,335,109 | A | * | 6/1982 | Hill ................................ 424/632 |
| 6,978,724 | B2 | * | 12/2005 | Anderson et al. ........... 106/18.32 |
| 7,427,316 | B2 | * | 9/2008 | Anderson et al. ........... 106/18.32 |
| 7,497,901 | B2 | * | 3/2009 | Anderson et al. ........... 106/18.32 |
| 2004/0016909 | A1 | * | 1/2004 | Zhang et al. ................... 252/380 |
| 2006/0078686 | A1 | * | 4/2006 | Hodge et al. .................. 427/440 |
| 2007/0163465 | A1 | | 7/2007 | Anderson et al. |

FOREIGN PATENT DOCUMENTS

WO WO2007079212 * 7/2007 ............. A01N 35/02

OTHER PUBLICATIONS

Banuett (Annual Reviews Genetics 1995 vol. 29 pp. 179-208).*
H. L. Yale, The Hydroxamic Acids, Chem. Rev., 1943, vol. 33:209-256.
M. Shiino et al., Synthesis of N-Substituted N-Nitrosohydroxylamines as Inhibitors of Mushroom Tyrosinase, Bioorganic and Medicinal Chemistry, 2001, vol. 95:1233-1240.

* cited by examiner

Primary Examiner — Patrick Ryan
Assistant Examiner — Aaron Greso
(74) Attorney, Agent, or Firm — Kevin S. Dobson

(57) ABSTRACT

This invention relates to wood preservatives containing copper complexes and calcium ions, zinc ions or calcium and zinc ions for protection of wood, cellulose, hemicellulose, lignocellulose, cellulosic materials and articles derived from cellulosic materials from decay caused by fungi. The calcium ions, zinc ions, or calcium and zinc ions improve the penetration of copper preservative agent into the interior of a treated material or article.

20 Claims, No Drawings

WOOD PRESERVATIVES CONTAINING COPPER COMPLEXES

This application claims priority under 35 U.S.C. §119(e) from, and claims the benefit of, U.S. Provisional Application No. 61/014,820, filed Dec. 19, 2007, which is by this reference incorporated in its entirety as a part hereof for all purposes.

TECHNICAL FIELD

This invention relates to wood preservative compositions containing copper complexes.

BACKGROUND

The decay of wood and other cellulosic materials by fungi, and the consumption of wood by termites, cause significant economic loss. Until recently, the most widely used wood preservative has been chromated copper arsenate (CCA). However, production of CCA for use in residential structures was prohibited as of January 2004 due to issues raised concerning the environmental impact and safety of arsenic and chromium used in CCA-treated lumber. As CCA replacements, arsenic-free and chromium-free wood preservatives have been developed.

A challenge is obtaining adequate penetration of wood by preservative agents, which typically occurs during pressure treatment of the wood by aqueous wood preservatives. Penetration of an effective amount of preservative agent to adequately protect wood from decay is needed. The acidic CCA wood preservative provides complete and thorough penetration of the preservative agents into wood. However, wood preservatives developed to replace CCA are typically basic systems such as ammoniacal copper quaternary (ACQ). Generally, in basic wood preservative solutions, the typically used copper ion preservative agent penetrates less well. This reduced penetration results in a dramatically decreasing gradient of preservative agent from the surface to the center of a treated article. To establish an effective concentration of preservative agent deep in the wood, high concentrations of preservative agents are needed in the wood preservative solution.

Thus there remains a need for wood preservative compositions which provide improved penetration of the wood preservative agent.

SUMMARY

One embodiment of this invention provides a composition of matter that includes a composition of matter comprising an aqueous solution of (a) a copper complex comprising copper and a chelating compound comprising at least two functional groups selected from the group consisting of amidoximes, hydroxamic acids, N-hydroxyureas, N-hydroxycarbamates, and N-nitroso-alkyl-hydroxylamines; (b) ammonia, ethanolamine or pyridine in an amount sufficient to solubilize the copper complex of (a); and (c) at least one divalent cation that is calcium ion, zinc ion or a combination thereof.

This invention also relates to a method for preparing a wood preservative composition comprising contacting an aqueous solution comprising a copper salt; at least one chelating compound comprising at least two functional groups selected from the group consisting of amidoxime, hydroxamic acid, N-hydroxyurea, N-hydroxycarbamate, and N-nitroso-alkyl-hydroxylamine; at least one divalent cation that is calcium ion, zinc ion or a combination thereof; and ammonia, ethanolamine, or pyridine.

This invention also relates to a process for preserving cellulosic material, or an article derived from cellulosic material, by contacting such materials with the wood preservative composition(s) of this invention.

This invention also relates to cellulosic material or articles treated by the preservation process of this invention.

This invention also relates to articles of wood, lumber, plywood, oriented strandboard, paper, cellulose, cotton, lignocellulose or hemicellulose which further comprise copper and a chelating compound comprising at least two functional groups selected from the group of amidoxime, hydroxamic acid, N-hydroxyurea, N-hydroxycarbamate, and N-nitroso-alkyl-hydroxylamine, and at least one divalent cation that is calcium ion, zinc ion or a combination of zinc ion and calcium ion.

DETAILED DESCRIPTION

Applicants have discovered that addition of calcium ions, zinc ions, or a combination of calcium ions and zinc ions to an aqueous wood preservative composition containing copper complexes of chelating compounds with two or more appropriate functional groups and solubilized by addition of ammonia, ethanolamine, or pyridine improves the penetration of the copper preservative agent into wood. With the addition of calcium ions, zinc ions, or a combination of calcium ions and zinc ions to the wood preservative solution, applicants discovered that an increased proportion of the copper wood preservative agent moved to internal portions of a piece of wood, compared to the same wood preservative solution without the ions. Due to this enhanced penetration of the composition, lower concentrations of copper preservative agent can be used to achieve: (i) adequate internal copper concentrations providing protection from fungal decay (ii) reduced cost and (iii) increased environmental friendliness of the wood preservative. Thus the present invention provides more effective and efficient preservatives for cellulosic material.

In the present wood preservatives, calcium ions and/or zinc ions are added to wood preservative compositions that are disclosed in U.S. Pat. No. 6,978,724 (which is by this reference incorporated in its entirety as a part hereof for all purposes), and an improvement in the penetration of the wood preservative agent is thereby provided. The wood preservative compositions disclosed in U.S. Pat. No. 6,978,724 contain solubilized copper complexes of copper ions and chelating compounds with at least two functional groups selected from the group of amidoxime, hydroxamic acid, N-hydroxyurea, N-hydroxycarbamate, and N-nitroso-alkyl-hydroxylamine. The copper complexes are solubilized in aqueous solution by the addition of ammonia, ethanolamine, or pyridine. Cellulosic materials can be treated with the wood preservative and upon loss or evaporation of ammonia, ethanolamine, or pyridine, these copper complexes become insoluble, thereby fixing (immobilizing) the copper ions within the material.

Cellulosic materials or articles derived from cellulosic materials that can be treated with a composition of this invention contain or are derived from cellulose, which is a polysaccharide that forms the main structural constituent of the cell wall in most plants, and is the primary constituent of most plant tissues and fibers. These cellulosic materials include wood and wood products such as lumber, plywood, oriented strandboard and paper, in addition to lignocellulose, cotton, hemicellulose and cellulose itself. References herein to the preservation of wood by the use of a composition of this invention, or by the performance of a process of this invention, or references to the usefulness of a composition hereof as a wood preservative, should therefore be understood to be references to the preservation of all types of cellulosic materials, not just wood alone.

The cellulosic materials, or articles derived therefrom, that can be treated with a composition of this invention or with a composition prepared by a process of this invention, are materials or articles involving cellulosic material that has been harvested and is no longer growing as a crop or in any other photosynthetic context, and is thus a suitable subject for preservation as provided by the composition and processes hereof. An advantageous effect of the compositions and processes hereof is that such harvested materials and articles, after the treatment hereof, are resistant to decay by fungal attack and are thus preserved.

Calcium ions and/or zinc ions are included in the wood preservative compositions in an amount that is effective for enhanced penetration of the copper wood preservative agent, as exemplified by a greater amount of copper detected in internal portions of a treated article as compared to when no calcium ions and/or zinc ions are included. Calcium ions and/or zinc ions are used in at least a 1:1 ratio with respect to copper ions in the wood preservative solution. More suitable is a ratio that is at least about 2:1 and most suitable is a ratio of at least about 4:1. Either calcium ions or zinc ions can be included, or a mixture of calcium and zinc ions can be used. Calcium ions and/or zinc ions are typically present in amounts from about 700 ppm to about 8000 ppm. Sources for calcium ions include Ca(II) salts such as calcium chloride, calcium hydroxide, calcium acetate, calcium carbonate and dolomitic limestone. Sources for zinc ions include Zn(II) salts such as zinc sulfate, zinc chloride, zinc acetate, zinc nitrate, and zinc carbonate.

The complex of copper and chelating compound in the present wood preservatives includes a chelating compound that has two or more multidentate chelating groups such as amidoxime, hydroxamic acid, N-hydroxyurea, N-hydroxycarbamate and N-nitroso-alkyl-hydroxylamine groups. These functional groups can be introduced by the methods described herein or by methods known in the art.

For example, an amidoxime is the oxime of an amide having the general formula $RC(=NOH)NH_2$. Amidoximes can be prepared by the reaction of nitrile-containing compounds with hydroxylamine. (Eqn. 1)

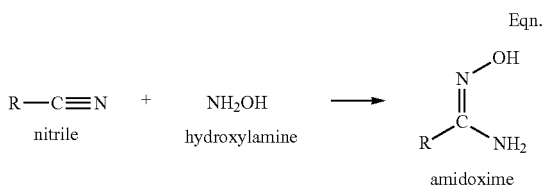

Eqn. 1

A hydroxamic acid is a class of amide compounds in which hydroxylamine is bonded to a carbonyl group through nitrogen. Its general structure is R—CO—NH—OH, wherein R is an organic residue, CO is a carbonyl group, and NH—OH is derived from hydroxylamine. Hydroxamic acids are also well known (H. L. Yale, "The Hydroxamic Acids", *Chem. Rev.*, 209-256 (1943)). Polymers containing hydroxamic acid groups are known and can be prepared by addition of hydroxylamine to anhydride groups of anhydride-containing copolymers, such as styrene-maleic anhydride copolymer or poly(vinylmethylether/maleic anhydride) copolymers, or by reaction of hydroxylamine with ester groups. Hydroxamic acid-containing polymers can also be prepared by acid-catalyzed hydrolysis of polymers that contain amidoxime groups, as further discussed in U.S. Pat. No. 3,345,344 (which is by this reference incorporated in its entirety as a part hereof for all purposes).

An N-hydroxyurea is a urea that is hydroxylated on one of the urea nitrogens. N-hydroxyurea (CASRN: 127-07-1) can be prepared by reaction of hydroxylamine with an isocyanate [A. O. Ilvespaa et al, *Chime (Switz.)* 18, 1-16 (1964)].

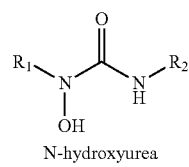

N-hydroxyurea

An N-hydroxycarbamate is a carbamate that is hydroxylated on the nitrogen. N-Hydroxycarbamates can be prepared by reaction of hydroxylamine with either a linear or cyclic carbonate [A. O. Ilvespaa et al, *Chimia (Switz.)* 18, 1-16 (1964)].

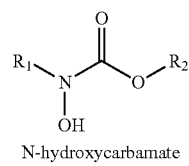

N-hydroxycarbamate

An N-nitroso-alkyl-hydroxylamine is a hydroxylamine that is nitrosylated on the nitrogen. N-Nitroso-alkyl-hydroxylamines can be prepared by nitrosation of alkyl hydroxylamines [M. Shiino et al, *Bioorganic and Medicinal Chemistry* 95, 1233-1240 (2001)].

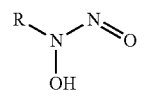

N-nitroso-alkyl-hydroxylamine

Preferred chelating compounds are those which contain two or more amidoxime and/or hydroxamic acid groups. The amidoxime functionality can be readily converted to the corresponding hydroxamic acid functionality in aqueous solution, a reaction that is catalyzed by acid.

A convenient route to this preferred class of chelating compounds (i.e. amidoximes and hydroxamic acids) is by adding hydroxylamine to the corresponding nitrile compound. There are several methods known for preparing nitrile-containing compounds, including cyanide addition reactions such as hydrocyanation, polymerization of nitrile-containing monomers to form polyacrylonitrile or copolymers of acrylonitrile with vinyl monomers, and dehydration of amides. Typical procedures for the syntheses of nitriles may be found in J. March, *Advanced Organic Chemistry*, 4th ed., John Wiley and Sons, NY, (1992).

A particularly useful route to nitriles is termed "cyanoethylation," in which acrylonitrile undergoes a conjugate addition reaction with protic nucleophiles such as alcohols and amines [Eqn. 2; see "The Chemistry of Acrylonitrile", 2$^{nd}$ Edition, American Cyanamid Co. Petrochemicals Dept., NY (1959) p 272]. Other unsaturated nitriles can also be used in place of acrylonitrile.

Eqn. 2

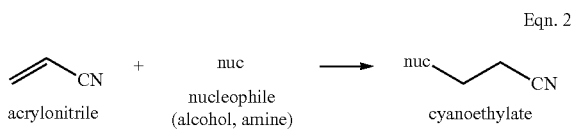

acrylonitrile + nucleophile (alcohol, amine) → cyanoethylate

Preferred amines for the cyanoethylation reaction are primary amines and secondary amines having 1 to 30 carbon atoms, and polyethylene amine. Alcohols can be primary, secondary, or tertiary. The cyanoethylation reaction (or "cyanoalkylation" using an unsaturated nitrile other than acrylonitrile) is preferably carried out in the presence of a cyanoethylation catalyst. Preferred cyanoethylation catalysts include lithium hydroxide, sodium hydroxide, and potassium hydroxide. The amount of catalyst used is typically between 0.05 mol % and 15 mol %, based on the unsaturated nitrile.

A wide variety of materials can be cyanoethylated. The cyanoethylates can be derived from the reaction of acrylonitrile with carbohydrates such as regenerated cellulose, dextran, dextrin, gums (guar, locust bean, honey locust, flame tree, tara, arabic, tragacanth, and karaya); starches (corn, potato, tapioca and wheat); or modified natural polymers such as cellulose xanthate, dimethylthiourethane of cellulose, ethyl cellulose, hydroxyethylcellulose, methylcellulose, and phenylthiourethane of cellulose. Other natural polymers that have been cyanoethylated include flax, jute, manila, sisal, and proteins such as blood albumin, casein, gelatin, gluten, soybean protein, wool, corn zein, and materials derived from such natural polymers. Pre-treatment of high molecular weight or water-insoluble carbohydrates and starches with enzymes can be used if necessary to increase the solubility of the amidoxime or hydroxamic acid copper complex in an aqueous ammonia, ethanolamine, or pyridine solution.

Synthetic polymers such as acetone-formaldehyde condensate, acetone-isobutyraldehyde condensate, methyl ethyl ketone-formaldehyde condensate, poly(allyl alcohol), poly (crotyl alcohol), poly(3-chloroallyl alcohol), ethylene-carbon monoxide copolymers, polyketone from propylene, ethylene and carbon monoxide, poly(methallyl alcohol), poly (methyl vinyl ketone, and poly(vinyl alcohol) have also been cyanoethylated, and can also serve as platforms for further modification into metal-binding polymers.

Cyanoethylated compounds can be derived from saccharides and saccharide-derivatives. A cyanoethylated compound is obtained from the cyanoethylation of materials selected from the group consisting of monosaccharides, disaccharides, hydrogenated derivatives of monosaccharides, hydrogenated derivatives of disaccharides and sugar alcohols. Preferably, the cyanoethylates are derived from sucrose and sorbitol, which are inexpensive and readily available.

The nitrile groups of these cyanoethylates or cyanoalkylates can be reacted with hydroxylamine to form the amidoxime or hydroxamic acid and then further reacted with ammoniacal or ethanolamine solutions of copper to give an amidoxime or hydroxamic acid copper complex that is a deep-blue, water-soluble solution. If hydroxylamine hydrochloride is used instead of hydroxylamine, sodium hydroxide, sodium carbonate or ammonium hydroxide can be used to neutralize the hydrochloric acid. Ammonium hydroxide is preferred.

The reaction to form the amidoxime or hydroxamic acid can be monitored by IR spectroscopy, where the loss of the nitrile peak at 2250 cm$^{-1}$ and appearance of a new peak at 1660 cm$^{-1}$ is indicative of amidoxime or hydroxamic acid formation. The IR spectra of an amidoxime and its corresponding hydroxamic acid are not easily distinguished in this region (1600-1700 cm$^{-1}$).

Hydroxylamine, hydroxylamine hydrochloride, and hydroxylamine sulfate are suitable sources of hydroxylamine in the present wood preservatives. When hydroxylamine hydrochloride is used as the source of hydroxylamine, a mixture of the amidoxime and hydroxamic acids is generally formed. Since both functional groups form complexes with copper, there is no need to separate the amidoxime and hydroxamic acid compounds before formation of the copper complex.

Preparation of the copper complexes of amidoximes or hydroxamic acids is carried out by adding a solution of Cu(II) salts to an aqueous solution of the amidoxime or hydroxamic acid. Suitable Cu(II) salts include copper sulfate, copper sulfate pentahydrate, cupric chloride, cupric acetate, and basic copper carbonate. The preferred copper salts are copper acetate and copper sulfate.

Typical copper complexes with amidoximes of sucrose and sorbitol, are shown in Diagram I (Cu-CE-AmSuc7) and Diagram II (Cu-CE-AmSorb6).

Diagram I

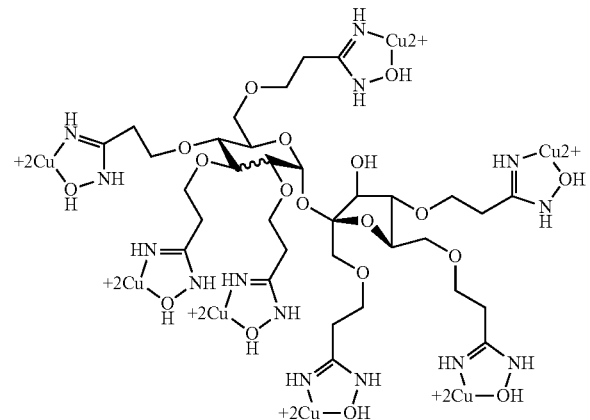

Diagram II

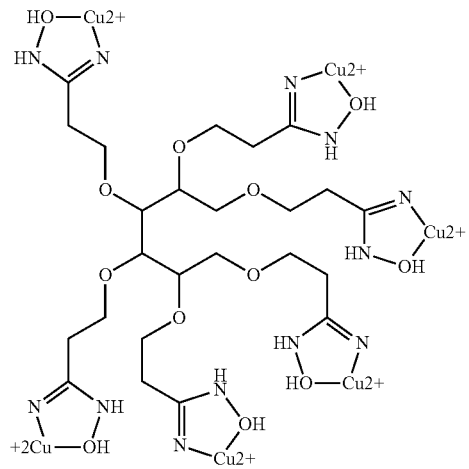

Upon addition of a Cu(II) solution to the amidoxime or hydroxamic acid, the solution turns a dark olive-green, and a white precipitate appears on standing. This precipitate can be redissolved by adding ammonium hydroxide, which turns the solution from olive-green to deep blue. To prepare wood preservation solutions free of insoluble precipitates, an ammoniacal, ethanolamine, or pyridine Cu(II) solution is added directly to the reaction solution containing amidoxime or hydroxamic acid without prior isolation of the amidoxime or hydroxamic acid.

The resulting solutions are diluted with water to known concentrations of Cu(II). Useful concentrations of copper in these solutions range from about 250 ppm to about 8000 ppm as determined, for example, by ion-coupled plasma determinations (ICP), and imbibed into wood under the standard pressure treatment process for waterborne preservative systems.

Polymers containing hydroxamic acid groups complex strongly with copper ion and the resulting complexes then bind tenaciously to cellulose. These polymeric compounds are useful for preserving wood.

Similar procedures to those described above can be used to prepare ammoniacal, ethanolamine, or pyridine Cu(II) solutions from compounds that contain at least two functional groups selected from the group of amidoxime, hydroxamic acid, N-hydroxyurea, N-hydroxycarbamate, and N-nitrosoalkyl-hydroxylamine functional groups.

Preservative Treatment

The present wood preservative solutions, which include calcium ions and/or zinc ions, can be applied to a cellulosic material by dipping, brushing, spraying, soaking, draw-coating, rolling, pressure-treating, or other known methods. The composition can be applied to achieve preservation of any cellulosic material, including for example wood, lumber, plywood, oriented strandboard, cellulose, hemicellulose, lignocellulose, cotton, and paper. Particularly efficacious is imbibing into wood under the standard pressure treatment process for waterborne preservative systems, in which a vacuum is applied before and/or after application of the preservative composition. Removal of air from the wood under vacuum, then breaking the vacuum in the presence of preservative solution, enhances penetration of the solution into the wood.

A particularly useful treatment process for wood is as described below. Wood, either dry or freshly cut and green, is placed in a chamber that is then sealed and evacuated in a regulated cycle which is determined by the species of wood. Generally, for Southern Yellow Pine (SYP) wood, the period of evacuation is about 30 minutes, during which time the pressure within the sealed chamber is brought to a level of about two inches of mercury or less. The evacuated pressure in the chamber can vary from 0.01 to 0.5 atm. The purpose of this step is to remove air, water and volatiles from the wood. The preservative composition is then introduced into the closed chamber in an amount sufficient to immerse the wood completely without breaking the vacuum to the air. Pressurization of the vessel is then initiated and the pressure maintained at a desired level by a diaphragm or other pump for a given period of time. Initially, the pressure within the vessel will decrease as the aqueous composition within the container penetrates into the wood. The pressure can be raised to maintain a desirable level of treatment throughout the penetration period. Stabilization of the pressure within the vessel is an indication that there is no further penetration of the liquid into the wood. At this point, the pressure can be released, the wood allowed to equilibrate with the solution at atmospheric pressure, the vessel drained, and the wood removed. In this part of the process, the pressures used can be as high as 300 psig, and are generally from about 50 to 250 psig.

Articles Incorporating Preservative Compositions

Articles of the present invention are those having been treated with a preservative composition described herein. Following treatment of articles such as those made from or by incorporating wood, lumber, plywood, oriented strandboard, paper, cellulose, cotton, lignocellulose, and hemicellulose, the ammonia in the ammoniacal solution of the preservative composition will dissipate. The copper complex is retained on and/or in the article.

The process of this invention for treating cellulosic material also includes a step of incorporating the cellulosic material, or a treated article derived from the cellulosic material, such as wood, into a structure such as a house, cabin, shed, burial vault or container, or marine facility, or into a consumable device such as a piece of outdoor furniture, or a truss, wall panel, pier, sill, or piece of decking for a building.

EXAMPLES

The advantageous attributes and effects of the compositions and processes hereof may be seen in a series of examples as described below. The embodiments of these processes on which the examples are based are representative only, and the selection of those embodiments to illustrate the invention does not indicate that materials, reactants, conditions, steps, techniques, or protocols not described in these examples are not suitable for practicing these processes, or that subject matter not described in these examples is excluded from the scope of the appended claims and equivalents thereof.

General Procedures

All reactions and manipulations except pressure treatment were carried out in a standard laboratory fume hood open to atmosphere. Deionized water was used where water is called for in the subsequent procedures. Sorbitol, acrylonitrile, lithium hydroxide monohydrate, hydroxylamine hydrochloride, 50% aqueous solution of hydroxylamine, copper sulfate pentahydrate, and Chromeazurol-S [CASRN:1667-99-8] were obtained from Sigma-Aldrich Chemical (Milwaukee, Wis.) and used as received. Concentrated ammonium hydroxide and glacial acetic acid were obtained from EM Science (Gibbstown, N.J.) and used as received. pH was determined with pHydrion paper from Micro Essential Laboratory (Brooklyn, N.Y.). Degree of substitution (DS) of the cyanoethylate is expressed in terms of equivalents of acrylonitrile used in the cyanoethylation step. IR spectra were recorded using a Nicolet Magna 460 spectrometer. Pressure treatment of southern yellow pine wood was performed in a high-pressure lab using stainless steel pressure vessels following the AWPA standard process (AWPA P5-01).

The meaning of abbreviations is as follows: "L" means liter(s), "mL" means milliliters, "g" means gram(s), "hr" means hour(s), "cm" means centimeter(s), "ppm" means parts per million, "mtorr" means millitor(s), "CE-Sorb" is cyanoethylated sorbitol, "CE-AmSorb" is the reaction product of hydroxylamine with CE-Sorb, "psi" means pounds/square inch, "IR" means infrared,"DS" is degree of substitution,"SYP" is "southern yellow pine", an acronym for closely related pine species that includes *Pinus caribaea Morelet, Pinus elliottii Englelm., Pinus palustris P. Mill., Pinus rigida P. Mill.*, and *Pinus taeda* L.

"AWPA" is the American Wood-Preserver's Association. AWPA standards are published in the "AWPA Book of Standards", AWPA, P.O. Box 5690, Granbury, Tex. 76049. The protocol for preservation of SYP stakes is based on AWPA Standard, Method E7-01, Sec. 4, 5, 6, and 7 and E11-97.

Cyanoethylatation of Sorbitol, DS=6.0 (CE-Sorb6).

A 1000 mL 3-necked round-bottomed flask equipped with a mechanical stirrer, reflux condenser, nitrogen purge, dropping funnel, and thermometer was charged with water (18.5 mL), lithium hydroxide monohydrate (1.75 g) and a first portion of sorbitol (44.8 g). The solution was heated to 42° C. with a water bath, with stirring, and a second portion of sorbitol (39.2 g) was added directly to the reaction flask. A first portion of acrylonitrile (100 mL) was then added to the reaction drop-wise via a 500 mL addition funnel over a period of 2 hr. The reaction was slightly exothermic, raising the temperature to 51° C. A final portion of sorbitol (32 g) was added for a total of 0.638 moles followed by a final portion of acrylonitrile (190 mL) over 2.5 hr, keeping the reaction temperature below 60° C. A total of 4.41 moles of acrylonitrile was used. The reaction solution was then heated to 50-55° C. for 4 hr. The solution was then allowed to cool to room temperature and the reaction was neutralized by addition of acetic acid (2.5 mL). Removal of the solvent under reduced pressure gave the product as a clear, viscous oil (324 g).

The IR spectrum showed a peak at 2251 $cm^{-1}$, indicative of the nitrile group.

Reaction of CE-Sorb6 with Hydroxylamine Hydrochloride to Prepare CE-AmSorb6

A 1000 mL three-necked round-bottomed flask was equipped with a mechanical stirrer, condenser, and addition funnel under nitrogen. CE-Sorb6 (14.77 g, 29.5 mmol) and water (200 mL) were added to the flask and stirred. In a separate 500 mL Erlenmeyer flask, hydroxylamine hydrochloride (11.47 g, 165 mmol, 5.6 eq) was dissolved in water (178 mL) and then treated with ammonium hydroxide (22.1 mL of 28% solution, 177 mmol, 6.0 eq) for a total volume of 200 mL. The hydroxylamine solution was then added in one portion directly to the mixture in the round-bottomed flask at room temperature. The mixture, having pH=8-9, was stirred and heated at 80° C. for 2 hr and then allowed to cool to room temperature.

The IR spectrum indicated loss of most of the nitrile peak at 2250 $cm^{-1}$ and the appearance of a new peak at 1660 $cm^{-1}$, indicative of the amidoxime or hydroxamic acid.

Example 1

Preparation of CE-AmSorb6 Amidoxime Copper Complex with Calcium Ion as Preservative A solution of 93.32 g of copper acetate monohydrate in 756 g of water was prepared. A solution of 354.4 g of calcium acetate monohydrate in 660 g of water was prepared. A solution of 100.52 g of CE-AmSorb6 (prepared as described above in General Methods) in 247 g water was prepared. The two salt solutions were added to a carboy. Then the CE-AmSorb6 solution was added. A deep green solution resulted. To the green solution was added 1000 g of 28% w/w ammonia dissolved in water. The solution color turned blue. To the resulting solution enough water was added to give a final solution weight of 20,000 g.

Example 2

Penetration of CE-AmSorb6 Amidoxime Copper Complex with Calcium Ion Preservative Four stakes measuring 1.5"×1.5"×38" (3.8 cm×3.8 cm×96.5 cm) were pressure treated with a control solution prepared as above but not containing calcium acetate. The stakes were cut at the 19" (48.3 cm) midpoint and then duplicate cross-sections 0.25" (0.64 cm) thick were cut from the center end of the stakes to give whole sections; the whole sections were weighed. Then from the center end of the cut stakes approximately 0.25" was cut away from the outside of the stakes to reveal a core section. Duplicate core sections were then cut into 0.25" thick core samples; the core samples were weighed. The samples were then dried over night at 60° C. and then asked at 580° C. for 24 hours. The ash samples were titrated iodometrically as described in US 2007/163,465 (which is by this reference incorporated in its entirety as a part hereof for all purposes) to determine the amount of copper in the samples. The ratio of the relative amount of copper in the core sections compared to the relative amount of copper in the whole sections was expressed as a percent and this percent is the penetration of the preservative into wood. The average penetration of the preservative prepared above without calcium ion was 66.8%. A similar test using the preservative solution prepared as above and containing calcium ion indicated a penetration of 80.9%.

What is claimed is:

1. A composition of matter comprising an aqueous solution consisting essentially of:
    (a) a copper complex comprising copper and a chelating compound comprising at least two functional groups selected from the group consisting of amidoximes, hydroxamic acids, N-hydroxyureas, N-hydroxycarbamates, and N-nitroso-alkyl-hydroxylamines;
    (b) ammonia, ethanolamine or pyridine in an amount sufficient to solubilize the copper complex of (a); and
    (c) calcium ion in an amount ranging from about 700 ppm to about 8000 ppm.

2. The composition of claim 1 wherein the functional groups are selected from the group consisting of amidoximes and hydroxamic acids.

3. The composition of claim 1 wherein the functional groups are selected from the group consisting of amidoximes and hydroxamic acids that are derived from cyanoethyl groups of a cyanoethylated compound.

4. The composition of claim 3 wherein the cyanoethylated compound is derived from the cyanoethylation of synthetic polymers selected from the group consisting of acetone-formaldehyde condensates; acetone-isobutyraldehyde condensates; methyl ethyl ketone-formaldehyde condensates; poly(allyl alcohol); poly(crotyl alcohol); poly(3-chloroallyl alcohol); ethylene-carbon monoxide copolymers; polyketones from propylene, ethylene and carbon monoxide; poly (methallyl alcohol); poly(methyl vinyl ketone); and poly(vinyl alcohol).

5. The composition of claim 3 wherein the cyanoethylated compound is derived from the cyanoethylation of materials selected from the group consisting of saccharides and saccharide derivatives.

6. The composition of claim 5 wherein the saccharides and saccharide-derivatives are selected from the group consisting of sucrose, glycerol and sorbitol.

7. A process for preparing a wood preservative composition, comprising contacting and admixing an aqueous solution consisting essentially of a copper salt; at least one chelating compound comprising at least two functional groups selected from the group consisting of amidoxime, hydroxamic acid, N-hydroxyurea, N-hydroxycarbamate, and N-nitroso-alkyl-hydroxylamine; calcium ion in an amount ranging from about 700 ppm to about 8000 ppm; and ammonia, ethanolamine or pyridine.

8. A process comprising contacting a cellulosic material, or an article derived from cellulosic material, with the composition of claim 1.

9. The process of claim 8, wherein the cellulosic material, or the article derived from cellulosic material, is selected from the group consisting of wood, lumber, plywood, oriented strandboard, cellulose, hemicellulose, lignocellulose, cotton, and paper.

10. The process of claim 8 which comprises dipping, brushing, spraying, draw-coating, rolling, or pressure-treating the cellulosic material, or the article derived from cellulosic material, with the composition of claim 1.

11. The process of claim 8, wherein the composition of claim 1 is adsorbed on and/or absorbed in the cellulosic material or an article derived from the cellulosic material.

12. The process of claim 8, wherein the article derived from cellulosic material comprises wood or lumber, and the process further comprises subjecting the wood or lumber to vacuum both before and after contacting the wood or lumber with the composition of claim 1.

13. A process comprising contacting a cellulosic material, or an article derived from cellulosic material, with a composition prepared by the process of claim 7.

14. The process of claim 13, wherein the cellulosic material, or the article derived from cellulosic material, is selected from the group consisting of wood, lumber, plywood, oriented strandboard, cellulose, hemicellulose, lignocellulose, cotton, and paper.

15. The process of claim 13 which comprises dipping, brushing, spraying, draw-coating, rolling, or pressure-treating the cellulosic material, or the article derived from cellulosic material, with a composition prepared by the process of claim 7.

16. The process of claim 13, wherein the article derived from cellulosic material comprises wood or lumber, and the process further comprises subjecting the wood or lumber to vacuum both before and after contacting the wood or lumber with a composition prepared by the process of claim 7.

17. The process of claim 13, wherein a composition prepared by the process of claim 7 is adsorbed on and/or absorbed in the cellulosic material or an article derived from the cellulosic material.

18. A cellulosic material or an article produced by the process of claim 8 wherein the article is selected from the group consisting of wood, paper, cellulose, cotton, lignocellulose and hemicellulose.

19. A cellulosic material or an article produced by the process of claim 13 wherein the article is selected from the group consisting of wood, paper, cellulose, cotton, lignocellulose and hemicellulose.

20. An article comprising:
(a) wood, lumber, plywood, oriented strandboard, paper, cellulose, cotton, lignocellulose or hemicellulose;
(b) a copper complex comprising copper and a chelating compound comprising at least two functional groups selected from the group consisting of amidoximes, hydroxamic acids, N-hydroxyureas, N-hydroxycarbamates, and N-nitroso-alkyl-hydroxylamines; and
(c) calcium ion in an amount ranging from about 700 ppm to about 8000 ppm;
wherein the article is obtained after the component of part (a) is treated with the aqueous solution of claim 1.

* * * * *